United States Patent
Steinebach

(10) Patent No.: US 9,664,670 B2
(45) Date of Patent: May 30, 2017

(54) METHOD FOR ASCERTAINING A TRANSMISSION VALUE

(71) Applicant: Siemens Healthcare Diagnostics Products GmbH, Marburg (DE)

(72) Inventor: Wolfgang Steinebach, Salz (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 11 days.

(21) Appl. No.: 14/088,588

(22) Filed: Nov. 25, 2013

(65) Prior Publication Data

US 2014/0147928 A1 May 29, 2014

(30) Foreign Application Priority Data

Nov. 27, 2012 (EP) .................................... 12194367

(51) Int. Cl.
  *G01N 21/59* (2006.01)
  *G01R 23/167* (2006.01)
  *G01N 33/50* (2006.01)

(52) U.S. Cl.
  CPC ......... *G01N 33/5002* (2013.01); *G01N 21/59* (2013.01); *G01N 2201/0696* (2013.01)

(58) Field of Classification Search
  CPC ............... G01N 33/5002; G01N 21/59; G01N 2201/0696
  USPC .......................... 250/343, 373; 356/300–334; 422/82.05–82.09; 436/164–172
  See application file for complete search history.

(56) References Cited

U.S. PATENT DOCUMENTS

| 3,973,848 | A | 8/1976 | Jowett et al. |
| 7,446,694 | B1 * | 11/2008 | Ahmed et al. ................ 341/160 |
| 2004/0124377 | A1 | 7/2004 | Chiang |
| 2007/0253866 | A1 | 11/2007 | Rousseau |
| 2009/0306487 | A1 * | 12/2009 | Crowe et al. ................ 600/322 |

FOREIGN PATENT DOCUMENTS

| CN | 101002099 A | 7/2007 |
| CN | 101484065 A | 7/2009 |
| CN | 102435325 A | 5/2012 |

OTHER PUBLICATIONS

Langlois, JM Pierre, Dhamin Al-Khalili, and Robert J. Inkol. "Polyphase filter approach for high performance, FPGA-based quadrature demodulation." Journal of VLSI signal processing systems for signal, image and video technology 32.3 (2002): 237-254.*
Chinese Search Report of Chinese Patent Application No. 2013106037768 dated Aug. 10, 2016.

* cited by examiner

*Primary Examiner* — Robert Eom
(74) *Attorney, Agent, or Firm* — Dugan & Dugan, PC

(57) ABSTRACT

The invention is in the field of in vitro diagnostics and relates to a method for ascertaining a transmission value for a light signal that is pulsed at a frequency through a specimen in an automatic analysis appliance. It also relates to a transmission measurement apparatus for an automatic analysis appliance, comprising a light source that is pulsed at a frequency and a photodetector having a downstream A/D converter.

10 Claims, 3 Drawing Sheets

METHOD FOR ASCERTAINING A TRANSMISSION VALUE

The invention is in the field of in vitro diagnostics and relates to a method for ascertaining a transmission value for a light signal that is pulsed at a frequency through a specimen in an automatic analysis appliance. It also relates to a transmission measurement apparatus for an automatic analysis appliance, comprising a light source that is pulsed at a frequency and a photodetector having a downstream A/D converter.

Numerous detection and analysis methods for determining physiological parameters in body fluid specimens such as blood, plasma, serum or urine or in other biological specimens are today performed in automated fashion in appropriate analysis appliances.

Today's analysis appliances are capable of performing a multiplicity of various types of detection reactions and analyses with a multiplicity of specimens. Popular analysis appliances, as used in clinical laboratories or in blood banks, usually comprise an area for the supply of specimen vessels that contain the primary specimens to be analyzed. For the purpose of feeding the specimen vessels into the analysis appliance, a transport system is usually provided that first of all transports the specimen vessels to a specimen identification device that records specimen-specific information affixed to a specimen vessel and forwards it to a memory unit. Next, the specimen vessels are transported to a specimen collection station. There, a specimen pipetting device is used to collect at least one aliquot of the specimen fluid from a specimen vessel and to transfer it to a reaction vessel.

The reaction vessels are usually disposable cuvettes that are kept available in a cuvette container in the analysis appliance and that are automatically transferred from the storage container to defined uptake positions. The reagents that are required for providing various types of test-specific reaction mixtures are situated in reagent containers that are stored in a reagent station. The reagent containers are supplied to the analysis appliance either automatically in a similar fashion to the specimen vessel feeding or manually.

The reagent station usually has a cooling unit in order to ensure that the reagents can be kept for as long as possible. A reagent pipetting device, which incidentally frequently has a heating apparatus, is used to transfer an aliquot of one or more reagents to a reaction vessel that already contains the specimen to be examined. Depending on the nature of the biochemical reaction that is set in motion through the addition of the reagents to a specimen, a different length of incubation time for the reaction mixture may be necessary. In any case, the reaction vessel containing the reaction mixture is finally supplied to a measurement system that measures a physical property of the reaction mixture.

The measurement result is again forwarded to a memory unit by the measurement system and evaluated. Next, the analysis appliance delivers specimen-specific measured values to a user by means of an output medium, such as a monitor, a printer or a network connection.

Measurement systems that are based on photometric (e.g. turbidimetric, nephelometric, fluorometric or luminometric) measurement principles are particularly widespread. These methods allow the qualitative and quantitative detection of analytes in liquid samples without needing to provide additional separation steps. The determination of clinically relevant parameters, such as the concentration or the activity of an analyte, is frequently accomplished by simultaneously or successively mixing an aliquot of a body fluid from a patient with one or more test reagents in the reaction vessel, which sets in motion a biochemical reaction that brings about a measurable alteration in an optical property of the test mixture. The photometry examines and uses the attenuation of a luminous flux during the transmission by an absorbent and/or dispersive medium. Depending on the nature of the biochemical or biophysical reaction initiated, different photometric measurement methods can be used that allow the measurement of a turbid liquid test mixture.

Turbidimetric methods involve the turbidity or the optical density of a solution or dispersion (suspension) being measured using the light attenuation or extinction of a beam of light passing directly through the dispersion (suspension). The transmission of the beam of light is captured by means of a photodetector that produces a voltage curve associated with the intensity of the light signal transmitted by the specimen.

To improve the signal-to-noise ratio and to reject low-frequency noise, photodetectors frequently involve the use of a lock-in amplifier. This involves a modulated measurement signal, i.e. a pulsed light signal sent through the specimen and received by the photodetector, being supplied via a bandpass filter to a multiplier that modulates the measurement signal with a phase-coupled reference signal at the same frequency and, following low-pass filtering, produces an output signal proportional to the amplitude of the modulated input signal.

Such a lock-in amplifier can also be implemented in digital systems such as FPGAs (field programmable gate arrays), i.e. integrated circuits. In this case, the measurement signal is first of all supplied to an A/D converter that ascertains a plurality of sample values for the voltage curve from the photometer. In this case, the same block structures from an analog circuit are implemented by digital blocks. However, this requires various units for signal processing, such as bandpass filters, multipliers and low-pass filters, to be produced. Therefore the system becomes comparatively complex, and an increased quantity of logic elements is required.

It is therefore an object of the invention to specify a method for ascertaining a transmission value and also a transmission measurement apparatus of the type mentioned at the outset that have the principle and the advantages of the lock-in amplifier in a digital implementation without bringing about an increased need for logic elements.

In respect of the method, the invention achieves the object by virtue of the method comprising the following steps:
a) a voltage curve associated with the intensity of the light signal transmitted by the specimen is produced,
b) a plurality of sample values for the voltage curve are ascertained,
c) a first voltage value associated with a light pulse is ascertained from a number of sample values, and a second voltage value associated with a dark time between two light pulses is ascertained from a number of sample values, wherein the sample values for ascertaining a second voltage value associated with a dark time between two light pulses are offset from the sample values for ascertaining a first voltage value associated with a light pulse by an integer multiple of a half-period corresponding to the frequency of the pulsed light signal, and
d) the second voltage value is subtracted from the first voltage value.

The difference obtained in step d) is proportional to the transmission value.

In this case, the invention is based on the consideration that, in the case of a simply connected signal and reference source, the lock-in method ultimately involves the multiplier performing simple multiplication of the voltage curve ascertained from the useful signal by the factor +1 and −1 on the basis of the phase of the signal that has been subjected to square-wave modulation. Signal components with a useful signal content, i.e. those from light pulses are in this case multiplied by +1, and signal components without a useful signal, i.e. from dark times between the light pulses, are multiplied by −1. If both components contain low-frequency noise components or DC components, they are removed following the multiplication by means of low-pass filtering. In this case, the low-pass filtering acts as an integrator element over a plurality of signal periods, so that ultimately summation takes place over the negative zero-signal noise components and the positive signal components. This outcome is also achieved when a voltage value that corresponds to a dark time is subtracted directly from a voltage value that corresponds to a light pulse. This means that the multiplication unit is no longer required for the signal processing.

Sample values used for the first voltage value and sample values used for the second voltage value are offset by an integer multiple of a half-period corresponding to the frequency of the pulsed light signal and hence have a firm phase correlation. This allows continual sampling of the signal or the voltage curve associated with the signal at equal intervals, the sample values being selected specifically for the signal-plus-noise component and for the pure noise component by means of the correlation to the frequency and phase of the light pulses. This produces a continually low-noise result signal.

In one advantageous refinement, sample values in a prescribed transition region between light pulse and dark time are rejected in step c), i.e. during the ascertainment of the voltage values that are associated with a light pulse or a dark time. This relates to sample values that fall into the rising or falling edge of the signal and hence do not yield stable signal values. Rejection of such signals improves the precision of the result.

Advantageously, the respective dark time for which the sample value is used for the second voltage value follows the respective light pulse for which the sample value is used for the first voltage value directly or precedes the respective light pulse directly. Firstly, subtraction of successive light pulses and dark times requires the least technical complexity, and secondly successive light pulses and dark times are most likely exposed to the same disturbance sources, which means that subtraction filters out the disturbance sources in optimum fashion, which increases the quality of the result.

In a further advantageous refinement, steps b), c) and d) are cyclically repeated and a mean value is formed over the values ascertained in step d). In this case, the mean value formation filters further disturbance components from the result, which means that an even better quality result is achieved.

Preferably, an inventive method for determining a transmission value is used for determining the concentration or activity of at least one analyte in a specimen. To this end, the concentration or activity of the analyte is determined by using at least one transmission value, which in turn is determined using the method according to the invention.

The invention therefore also relates to a method for determining the concentration or activity of at least one analyte in a specimen, wherein the concentration or activity of the at least one analyte is determined by using at least one transmission value that is determined using a method according to the invention. In particular, the invention relates to a method for determining the concentration or activity of at least one analyte in a body fluid specimen, preferably in a body fluid specimen from the group comprising full blood, blood plasma, serum, liquor or urine.

A transmission measurement apparatus according to the invention comprises means for carrying out the method described.

In respect of the transmission measurement apparatus, the object is achieved by virtue of the A/D converter having a sampling frequency that corresponds to an even multiple of the frequency of the pulsed light signal, and the transmission measurement apparatus having an integrated circuit that is connected downstream of the A/D converter and that is designed to associate sample values from the A/D converter with a light pulse or with a dark time between two light pulses on the basis of the frequency and phase, to delay the sample values associated with light pulses or the sample values associated with dark times by a half-period corresponding to the frequency and to subtract resultant simultaneous sample values from one another. In one advantageous refinement, the A/D converter and the downstream integrated circuit are integrated in one component.

The invention also therefore relates to a transmission measurement apparatus for an automatic analysis appliance, comprising a light source that is pulsed at a frequency, a photodetector having a downstream A/D converter with a sampling frequency that corresponds to an even multiple of the frequency of the pulsed light source, and also an integrated circuit that is connected downstream of the A/D converter and that is designed to i) associate sample values from the A/D converter with a light pulse or with a dark time between two light pulses on the basis of the frequency of the pulsed light source and phase, and
ii) delay the sample values associated with the light pulses or the sample values associated with the dark times by an integer multiple of a half-period corresponding to the frequency of the pulsed light source, and
iii) subtract resultant simultaneous sample values from one another.

Advantageously, the sampling frequency has at least four times the value of the frequency of the pulsed light source. The effect achieved by this is oversampling, with two respective sample values already being able to be associated with each light pulse and each dark time at a four-times sampling frequency.

In a further advantageous refinement, the integrated circuit is designed to form a mean value over the subtracted simultaneous sample values. The increase in the digital resolution particularly in connection with the mean value formation further improves the quality of the result signal.

In a further advantageous refinement, the integrated circuit contains a field programmable gate array (FPGA). This is advantageous particularly because in some known automatic analysis appliances such FPGAs are used for the execution of other tasks, such as for the implementation of a processor system, for the evaluation of measurement signals or for the control of motors or various actuators, and are therefore already contained in the appliance. If an FPGA is thus already present, it is a simple matter to implement further functions, such as the method described here, without the need for redevelopment of a microprocessor circuit. This increases flexibility in respect of changes in the case of desired new properties of an automatic analysis appliance. Furthermore, it is advantageous that complex functions can be implemented at a much higher speed in FPGAs than in microprocessors.

Advantageously, an automatic analysis appliance comprises a transmission measurement apparatus as described.

The advantages attained with the invention are particularly that the use of time shifting, subtraction and mean value formation for reducing noise components in the photodetector signal from a transmission measurement apparatus allows simplification of the structure without complex signal processing blocks, such as filters or multipliers. This makes it possible to resort to inexpensive logic, e.g. simple algebraic operations. The solution is less expensive not only in comparison with DSP (digital signal processing) design but also in comparison with analog technology. There is no need for complex trimming operations, such as gain, phase or filter characteristic. Drift in the signal as in the case of analog methods is likewise not to be expected.

DESCRIPTION OF THE FIGURES

The invention is explained in more detail with reference to a drawing, in which.

Identical parts are provided with the same reference symbols throughout the figures.

Figure 1:
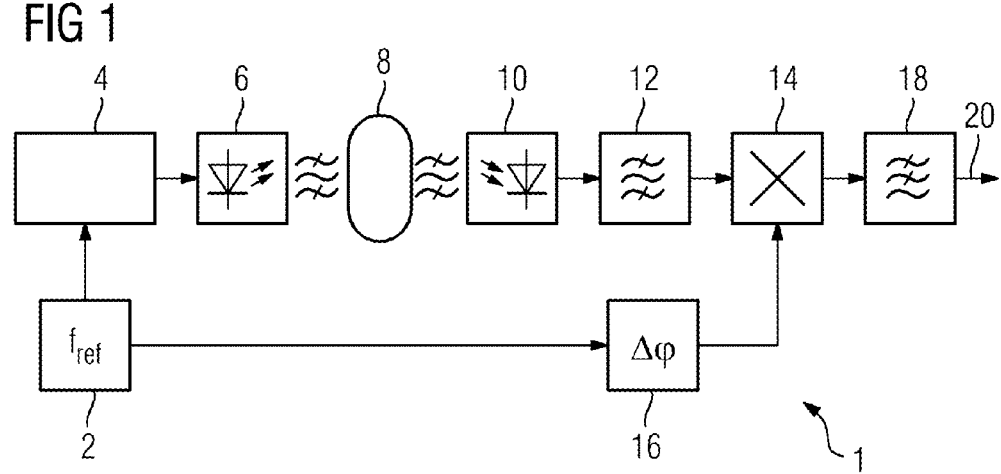
FIG. 1 shows a transmission measurement apparatus with a lock-in amplifier based on the prior art.

The transmission measurement apparatus 1 shown in FIG. 1 shows the manner of operation of a standard lock-in amplifier. It first of all has a frequency generator 2 that has a downstream modulator 4. The modulator 4 modulates the signal from the frequency generator 2, which signal typically oscillates about a zero value, such that a uniform switch-on and switch-off oscillation is achieved for a light source 6, in this case a light-emitting diode. The light source 6 is therefore pulsed at the frequency of the frequency generator 2. Alternatively, it would also be possible to use a continuous light source 6 having a chopper wheel with an appropriate rotation frequency.

The light source 6 shines through a specimen 8, in the present case a blood specimen in an automatic analysis appliance that is not shown in more detail. In this case, the blood specimen is subjected to a chemical reaction, during which the absorption of the light from the light source 6 is intended to be ascertained by means of a transmission measurement. The transmitted light is captured by a photodetector 10.

The photodetector 10 first of all has a downstream bandpass filter 12, the transfer function of which has a maximum in the region of the frequency of the frequency generator 2. The bandpass filter 12 firstly filters out disturbing signal components outside the pulse frequency of the light source 6, and secondly takes the signal from the photodetector 10, which signal oscillates between zero and a maximum value, and produces a signal oscillating about zero again. This signal is multiplied in a multiplier 14 by the signal from the frequency generator 2, the latter signal being phase-shifted in a phase shifter 16. In this case, the phase shift is set such that a maximum output signal is achieved on the multiplier 14.

Finally, the output signal is supplied to a low-pass filter 18, which ultimately acts as an integrator and outputs a DC voltage signal as result signal 20. The result signal 20 is proportional to the transmission by the specimen 8 and is largely free of disturbing influences. The method shown in FIG. 1 is used particularly in order to increase the sensitivity for low signal levels. Influences from low-frequency noise (e.g. 1/f noise) and extraneous light (daylight, artificial lighting) are diminished.

Implementation of the transmission measurement apparatus 1 shown in FIG. 1 in digital systems such as FPGAs is fundamentally possible but requires comparatively complex digital implementation of the DSP modules such as bandpass filter 12, multiplier 14 and low-pass filter 18.

Figure 2:
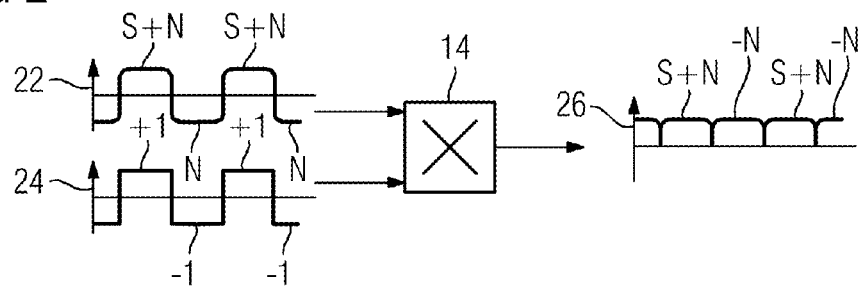
FIG. 2 shows the basic manner of operation of the known lock-in amplifier from FIG. 1 in the case of a simply connected signal.

FIG. 2 shows a simplified illustration of the manner of operation of the multiplier 14 in the case of a simply connected signal, such as from a pulsed light source 6 in an automatic analysis appliance. A phase shift is typically not to be expected. The photodetector signal 22 is multiplied by the square wave signal 24 from the frequency generator 2, which square wave signal oscillates between −1 and +1. Since the +1 ranges always correspond to the light pulses from the light source 6, signal components with a useful signal S are therefore always multiplied by +1, whereas signals from dark times, which contain only noise N, are multiplied by −1. This results in the output signal 26 with alternating S+N and −N ranges that is shown in FIG. 2. If both components contain low-frequency noise components or DC components, these are removed following the multiplication by means of low-pass filtering.

Figure 3:
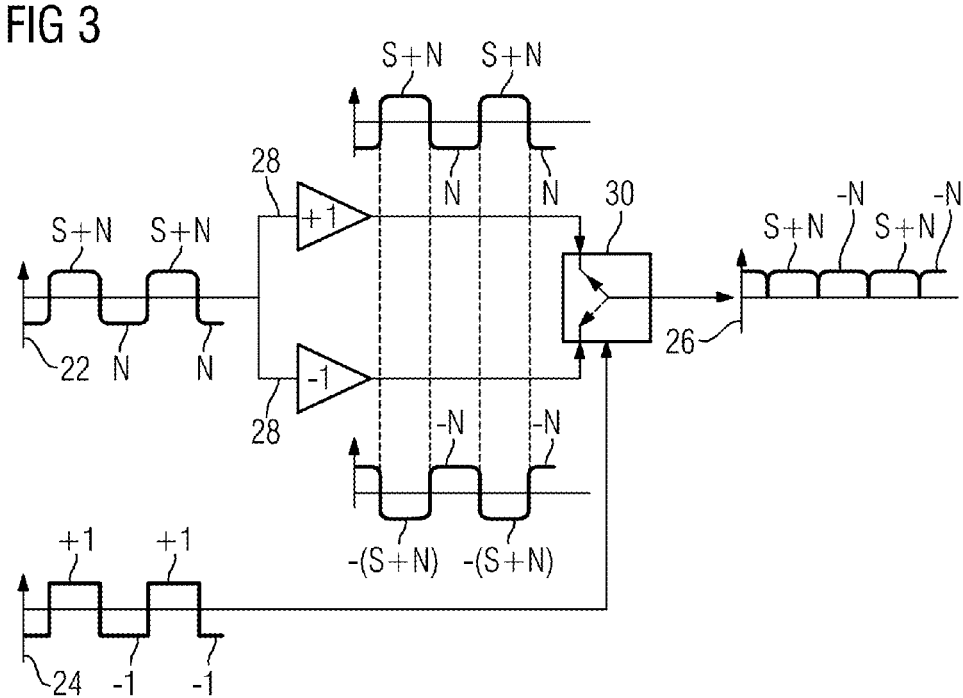
FIG. 3 shows a possible implementation of the manner of operation shown in FIG. 2.

In fact, the principle in FIG. 2 can be implemented by the circuit shown in FIG. 3. The photodetector signal is split into two branches 28, one of which is multiplied by −1. The corresponding signals are shown for each branch 28 in FIG. 3. The square wave signal 24 controls a switch 30 that switches between the two branches 28 at the frequency of the square wave signal 24. This produces the output signal 26 that is already shown in FIG. 2.

Subsequent low-pass filtering can be implemented as mean value formation over a plurality of periods in the simple case shown in FIGS. 2 and 3. In this context, the no-signal noise N is therefore ultimately subtracted from the useful signal with the noise component S+N. The output signal obtained is S=(S+N)−N.

Figure 4:
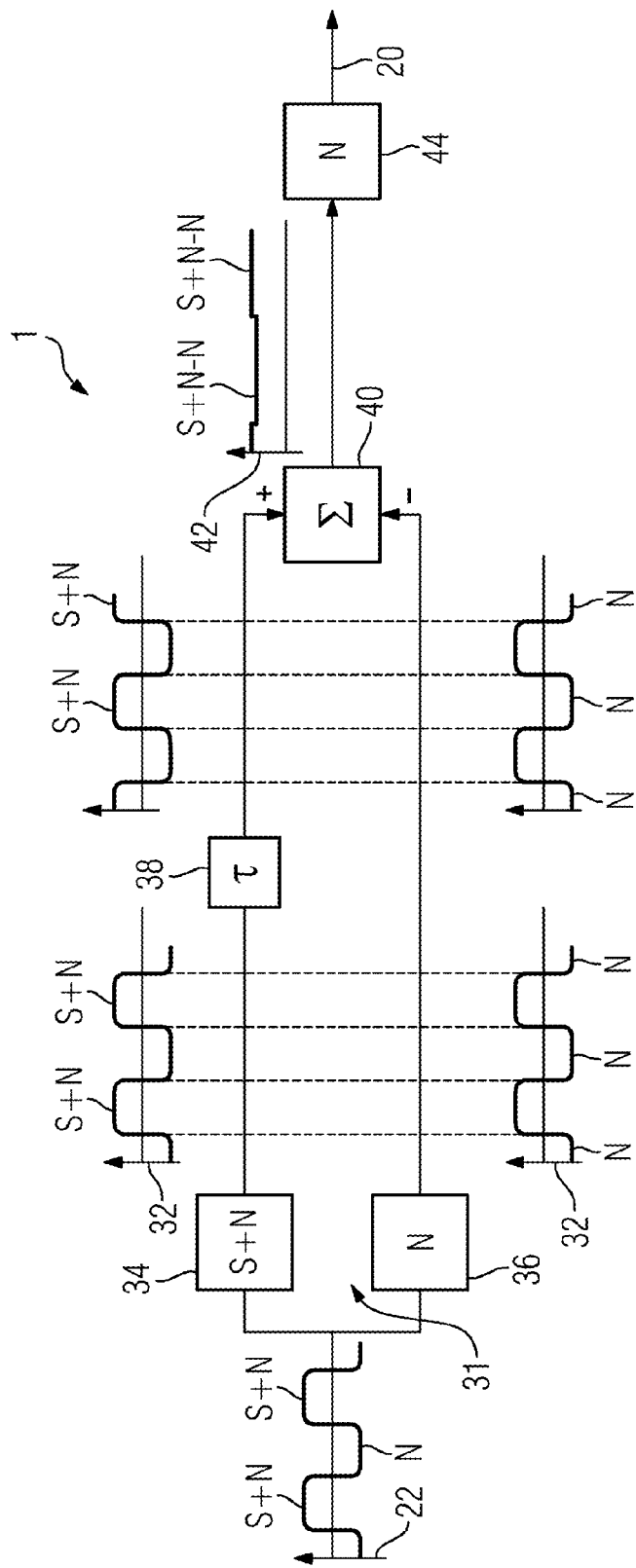
FIG. 4 shows a detail from a transmission measurement apparatus according to the invention with correlated oversampling.

Alternatively, this result is also achieved when the zero-signal noise component N is subtracted directly from the preceding or following signal component S. This means that a multiplier 14 is no longer necessary. A transmission measurement apparatus 1 operating on the basis of this principle has details shown from it in FIG. 4. The circuit shown in FIG. 4 is implemented on an integrated circuit, namely an FPGA.

The photodetector signal 22 is supplied to an A/D converter 31, which firstly performs sampling of the S+N ranges, and also of the N ranges. In the exemplary embodiment, the A/D converter 31 is in the form of an 18-bit A/D converter. The frequency of the light source is 45 kHz, and the A/D converter is designed for a 20-times sampling frequency, so that in each case ten sample values 32 per period are stored and processed as S+N sample values 34 and ten sample values 32 are stored as N sample values 36. Since the frequency of the A/D converter 31 is correlated to the frequency of the light source 6, the sample values 32 can be associated directly with a light pulse or a dark time. Sample values 32 that fall onto the rising or falling edge are ignored or rejected.

The oversampling of a lock-in period of twenty signal values in the exemplary embodiment by using four signal component values and four noise component values in each case already increases the result of the signal value calculation by the factor four, which corresponds to a two-bit digital resolution. Uncorrelated high-frequency noise is reduced by the factor root four, which results in a first improvement in the signal-to-noise ratio.

The S+N sample values 34 are delayed in a delay element 38 by a number of sample values 32 that corresponds to a half-period of the frequency of the light source 6. A subtractor element 40 is used to subtract simultaneous, delayed S+N sample values 34 and N sample values 36 from one another. In particular, this also makes it possible to dispense with bandpass filtering downstream of the photodetector 10. The output signal 42 from the subtractor element 40 is supplied to simple mean value formation 44 that can be set over N periods. In the exemplary embodiment, averaging takes place over 1024 lock-in periods, i.e. periods of the light source 6.

The circuit shown results in a corresponding increase in the resolution by 10 bits for the result signal 20 and in a further improvement in the signal-to-noise ratio of theoretically root 1024=32 (or 30 dB, 5 bits digital) for uncorrelated noise. Uncorrelated noise cannot be assumed under real conditions however, which means that the real resolution gain turns out lower. Measurements have yielded an equivalent resolution of approximately 22 to 23 bits in the exemplary embodiment, which corresponds to a signal-to-noise ratio of more than 130 dB. Sensitivity toward externally impinging extraneous light is very low in this case.

LIST OF REFERENCE SYMBOLS

1 Transmission measurement apparatus
2 Frequency generator
4 Modulator
6 Light source
8 Specimen
10 Photodetector
12 Bandpass filter
14 Multiplier
16 Phase shifter
18 Low-pass filter
20 Result signal
22 Photodetector signal
24 Square wave signal
26 Output signal
28 Branches
30 Switch
31 A/D converter
32 Sample values
34 S+N sample values
36 N sample values
38 Delay element
40 Subtractor element
42 Output signal
44 Mean value formation
S Useful signal
N Noise

The invention claimed is:

1. A transmission measurement apparatus for an automatic analysis appliance, comprising a light source pulsed at a frequency, a photodetector, an A/D converter with a sampling frequency that corresponds to an even multiple of the frequency of the light source, the A/D converter being connected downstream of the photodetector, and an integrated circuit connected downstream of the A/D converter and programmed to:

associate sample values from the A/D converter with a light pulse or with a dark time between two light pulses based on the frequency of the light source and a phase of the light source, delay the associated sample values by an integer multiple of a half-period corresponding to the frequency of the light source, and subtract the delayed sample values from one another; wherein:

the integrated circuit comprises no signal multiplier; and the transmission measurement apparatus has no bandpass filter connected downstream of the photodetector and no low pass filter connected downstream of the A/D converter.

2. The transmission measurement apparatus as claimed in claim 1, in which the sampling frequency has at least four times the value of the frequency of the light source.

3. The transmission measurement apparatus as claimed in claim 1, in which the integrated circuit is designed to form a mean value over the subtracted sample values.

4. The transmission measurement apparatus as claimed in claim 1, in which the integrated circuit contains a field programmable gate array (FPGA).

5. An automated analysis appliance having a transmission measurement apparatus as claimed in claim 1, wherein the integrated circuit comprises a delay element and a subtractor element, the delay element coupled to receive a first output of the A/D converter and the subtractor element coupled to receive an output of the delay element and a second output of the A/D converter.

6. A transmission measurement apparatus for an automatic analysis appliance, comprising a light source pulsed at a frequency, a photodetector, an A/D converter with a sampling frequency that corresponds to an even multiple of the frequency of the light source, the A/D converter being connected downstream of the photodetector, and an integrated circuit connected downstream of the A/D converter and programmed to:

associate sample values from the A/D converter with a light pulse or with a dark time between two light pulses based on the frequency of the light source and a phase of the light source, delay the associated sample values by an integer multiple of a half-period corresponding to the frequency of the light source, and subtract the delayed sample values from one another; wherein:

the integrated circuit comprises no signal multiplier and no low pass filter, and the integrated circuit is configured to provide a signal-to-noise ratio of more than 130 dB.

7. The transmission measurement apparatus as claimed in claim 6, in which the sampling frequency has at least four times the value of the frequency of the light source.

8. The transmission measurement apparatus as claimed in claim 6, in which the integrated circuit is designed to form a mean value over the subtracted sample values.

9. The transmission measurement apparatus as claimed in claim 6, in which the integrated circuit contains a field programmable gate array (FPGA).

10. An automated analysis appliance having a transmission measurement apparatus as claimed in claim 6, wherein the integrated circuit comprises a delay element and a subtractor element, the delay element coupled to receive a first output of the A/D converter and the subtractor element coupled to receive an output of the delay element and a second output of the A/D converter.

\* \* \* \* \*